United States Patent [19]

Bastian et al.

[11] 3,958,003
[45] May 18, 1976

[54] ORGANIC COMPOUNDS

[75] Inventors: Jean-Michel Bastian, Therwil; Klaus Hasspacher, Riehen; Michael Strasser, Basel, all of Switzerland

[73] Assignee: Sandoz Ltd., Basel, Switzerland

[22] Filed: May 2, 1975

[21] Appl. No.: 573,850

Related U.S. Application Data

[63] Continuation-in-part of Ser. No. 419,670, Nov. 28, 1973, Pat. No. 3,901,916, which is a continuation-in-part of Ser. No. 282,609, Aug. 21, 1972, abandoned.

[30] Foreign Application Priority Data

Nov. 28, 1972  Switzerland.................... 17291/72

[52] U.S. Cl. ............................................. 424/274
[51] Int. Cl.² ........................................ A61K 31/40
[58] Field of Search .............. 260/526.5 R; 424/274

Primary Examiner—Stanley J. Friedman
Attorney, Agent, or Firm—Gerald D. Sharkin; Robert S. Honor

[57] ABSTRACT

The present invention concerns new heterocyclic compounds of the formula:

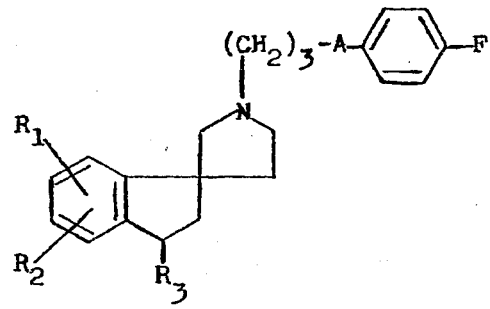

wherein
$R_1$ and $R_2$ are inter alia alkyl, chlorine or methoxy,
$R_3$ is hydroxy, alkylcarboxy or monoalkylcarbamoyloxy, and
A is protected or unprotected carbonyl.

The compounds possess analgesic and central nervous system depressant properties.

29 Claims, No Drawings

ORGANIC COMPOUNDS

This application is a continuation-in-part of our copending application Ser. No. 419,670 filed Nov. 28, 1973 now U.S. Pat. No. 3,901,916, the whole contents of which are incorporated herein by reference which is in turn a continuation-in-part of our copending application Ser. No. 282,609 filed Aug. 21, 1972, now abandoned.

The present invention relates to new heterocyclic compounds.

The present invention provides compounds of formula I,

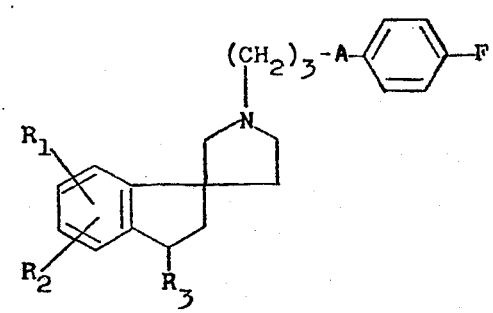

I wherein
- $R_1$ is hydrogen, alkyl of 1 to 3 carbon atoms, fluorine, chlorine, bromine or methoxy,
- $R_2$ is hydrogen, alkyl of 1 to 3 carbon atoms, chlorine or methoxy, or
- $R_1$ and $R_2$ are ortho one to another and together form a methylene dioxy group,
- $R_3$ is hydroxy, alkylcarboxy of 2 to 5 carbon atoms or monoalkylcarbamoyloxy of 2 to 5 carbon atoms, and
- A is carbonyl, 1,3-dioxolan-2-ylidene or 1,3-dioxan-2-ylidene.

The present invention also provides a process for producing a compound of formula I, comprising
a. reacting a compound of formula II,

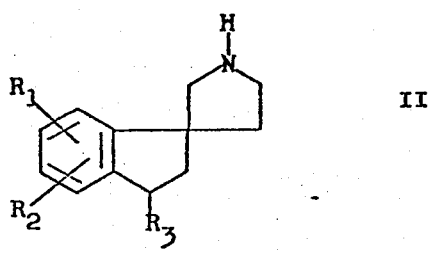

II wherein $R_1$, $R_2$ and $R_3$ are as defined above, with a compound of formula III,

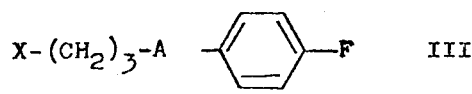

III wherein
- X is chlorine, bromine, iodine or an organic sulphonic acid radical, and
- A is as defined above and which when carbonyl, may be protected by ketal, thioxo or thioketal formation, and when required removing any carbonyl protecting groups from the resulting compound, or
b. reacting a compound of formula I$a$,

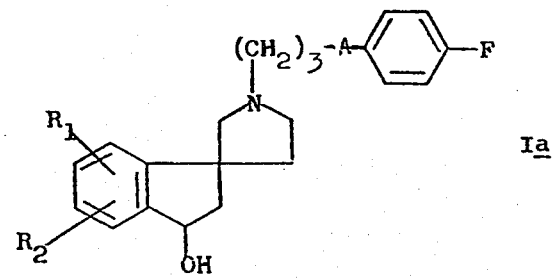

I$a$ wherein $R_1$, $R_2$ and A are as defined above, with a compound of formula IV$a$,

IV$a$ wherein
- $R_4$ is lower alkyl, and
- $X^I$ is chlorine, bromine or the acid radical of a carboxylic acid of 1 to 4 carbon atoms, to produce a compound of formula I$b$,

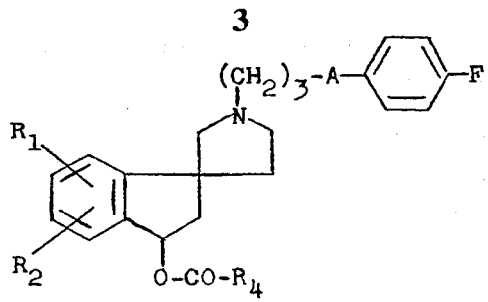

wherein $R_1$, $R_2$, $R_4$ and A are as defined above, or c. reacting a compound of formula Ia with a compound of formula IVb,

wherein $R_4$ is as defined above, to produce a compound of formula Ic,

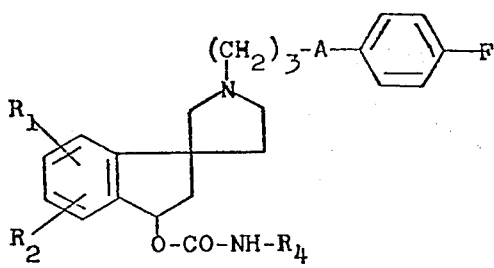

wherein $R_1$, $R_2$, $R_4$ and A are as defined above.

Process (a) may, for example, be effected by heating a compound of formula II with a compound of formula III in an inert organic solvent, e.g. an aromatic hydrocarbon such as benzene or toluene, a halogenated hydrocarbon such as chloroform, a cyclic ether such as tetrahydrofuran or dioxane, an alcohol such as ethanol, dimethyl formamide or acetone, to a temperature between preferably 50° and 150°C, conveniently with the addition of an acid-binding agent, e.g. an alkali metal carbonate such as sodium or potassium carbonate, or an organic base, e.g. pyridine or triethylamine. The reaction time may range between 1 and 70 hours. Suitable protective groups for the carbonyl function are, e.g., ketals which are capable of being removed at lower temperatures, preferably at a temperature of below 25°C, without the use of highly concentrated acids, such as optionally mixed ketals of suitable mono- or divalent alkyl alcohols, alkylthio alcohols or mixed alkyloxothio alcohols. It is preferred to use cyclic ketals having 5 or 6 ring members, especially dioxolane. The removal of the protective radical from the resulting compound after the reaction is complete, is effected in known manner, e.g. in the case of ketals by hydrolysis with a dilute mineral acid, e.g. with approximately 2 N hydrochloric acid, preferably at a temperature between 0 and approximately 25°C. Thioketals may be removed in known manner with mercury (II) chloride.

Process (b) may be effected in accordance with the usual methods for esterification, e.g. a compound of formula Ia may be reacted with an acid anhydride or halide of formula IVa, optionally in an inert organic solvent, e.g. an aromatic hydrocarbon such as benzene or toluene, or a cyclic ether such as dioxane, optionally with the addition of an acid-binding agent, e.g. an alkali metal bicarbonate or carbonate such as sodium bicarbonate, sodium carbonate or potassium carbonate, or an organic base such as pyridine or triethylamine, which may simultaneously serve as solvent, at a temperature between approximately 10° and 80°C. The reaction time may amount to 1 to 20 hours.

The production of a compound of formula Ic in accordance with process (c) may, for example, be effected by reacting a compound of formula Ia with an alkyl isocyanate of formula IVb, in an inert organic solvent, e.g. an aromatic hydrocarbon such as benzene or toluene, a halogenated hydrocarbon such as methylene chloride or chloroform, or a cyclic ether such as dioxane or tetrahydrofuran, for 1 to 50 hours at a temperature between approximately 10° and 80°C.

The compounds of formula I exist in free base and acid addition salt form. Acid addition salt forms may be produced from free base forms in manner known per se, e.g. by reaction thereof with a suitable acid, and vice versa.

The compounds of formula I also exist in isomeric forms since they possess two asymmetric centres at position 1 and 3 of the indan nucleus. Thus, for example, they may be isolated as the IRS,3RS or the IRS,3SR racemates. Such forms are embraced with the scope of formula I. Diastereoisomers may be separated from mixtures thereof in manner known per se, e.g. by fractional crystallization of suitable acid addition salt forms or by chromatography.

Furthermore, the processes (a), (b) and (c) of the invention are stereospecific in the sense that the configuration at the asymmetric centres at positions 1 and 3 of the indan nucleus of the starting materials remains intact and is not affected under the reaction conditions. As will be readily appreciated therefore, when final compounds of particular isomeric form are required, either separation of the final compounds obtained may be effected, or alternatively, starting materials of the desired isomeric forms may be employed.

The starting materials may, for example, be obtained as follows:

a'. A compound of formula II may, for example, be obtained by hydrogenolytic debenzylation of a compound of formula V,

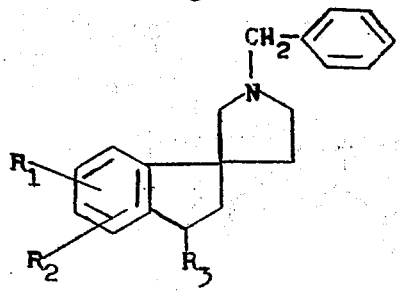

V wherein $R_1$, $R_2$ and $R_3$ are as defined above. Hydrogenation may, for example, be effected in the presence of a catalyst, preferably a palladium catalyst, in an inert organic solvent, e.g. ethyl acetate or a suitable alcohol such as ethanol.

b'. A compound of formula IIa,

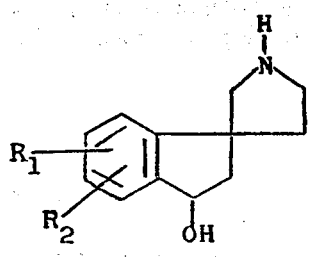

IIa wherein $R_1$ and $R_2$ are as defined above, may, for example, be obtained by reducing a compound of formula VI,

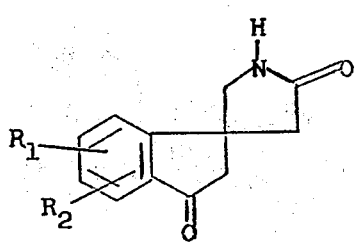

VI wherein $R_1$ and $R_2$ are as defined above. Reduction may, for example, be effected with a complex metal hydride, e.g. lithium aluminium hydride, in an inert organic solvent, e.g. an aromatic hydrocarbon such as benzene, or an ether such as tetrahydrofuran, dioxane, diethyl ether or dimethoxyethane. The reduction may be effected in two stages. Thus for example a compound of formula VI may first be reduced, e.g. with sodium borohydride in a suitable alcohol such as methanol, or an alcohol/ water mixture, or hydrogenolytically in the presence of a catalyst, e.g. platinum oxide, conveniently in a suitable alcohol, to obtain a compound of formula VIa,

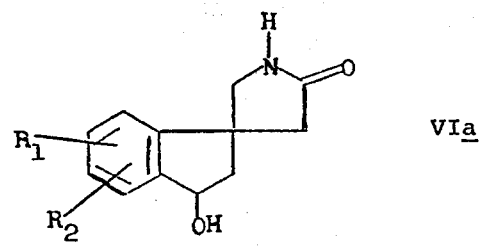

VIa wherein $R_1$ and $R_2$ are as defined above, and this may then be further reduced, e.g. with lithium aluminum hydride, to obtain a compound of formula IIa.

The above reductions may proceed with some stereochemical control such that the production of one diastereoisomeric form of the compounds of formula VIa or IIa, predominates depending on the nature of substituents $R_1$ and $R_2$ and the reduction conditions used, i.e. the reactions may, in some circumstances, be said to involve asymmetric induction. When mixtures of diastereoisomeric forms are obtained, they may be separated in known manner, e.g. by fractional crystallization or by chromatography.

c'. A compound of formula Vb,

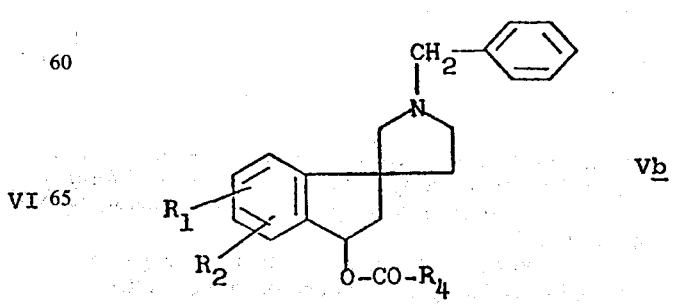

Vb wherein $R_1$, $R_2$ and $R_4$ are as defined above, may, for example, be obtained by reacting a compound of formula V$a$,

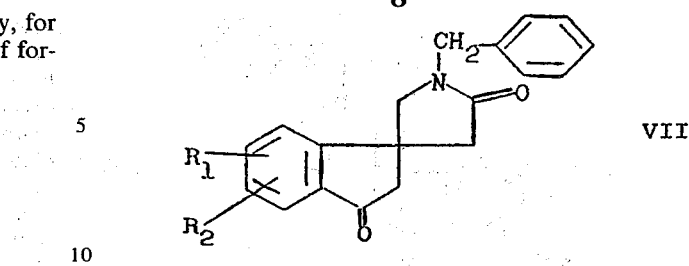

VII wherein $R_1$ and $R_2$ are as defined above, as described in process ($b'$).

f'. A compound of formula VII may, for example, be obtained by benzylating a compound of formula VI with a compound of formula VIII,

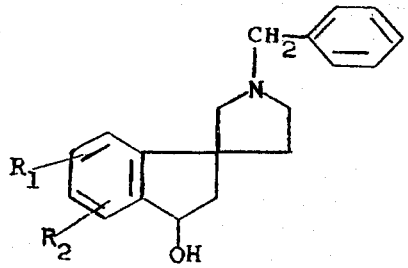

V$a$

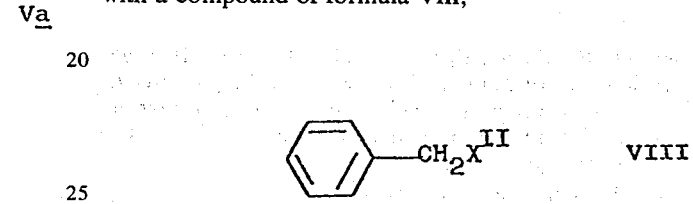

VIII wherein $X^{II}$ is chlorine or preferably bromine. Benzylation may, for example, be effected in an inert organic solvent, e.g. an aromatic hydrocarbon such as benzene or toluene, in the presence of a basic condensation agent, e.g. sodium amide.

wherein $R_1$ and $R_2$ are as defined above, with a compound of formula IV$a$, as described in process ($b$).

d'. A compound of formula V$c$, g'. A compound of formula VI may, for example, be obtained by cyclizing a compound of formula IX,

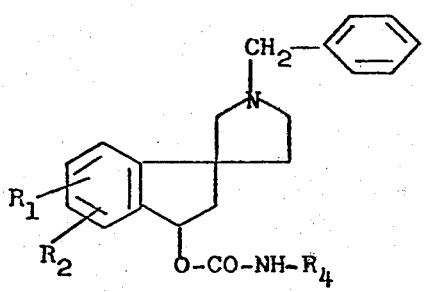

V$c$

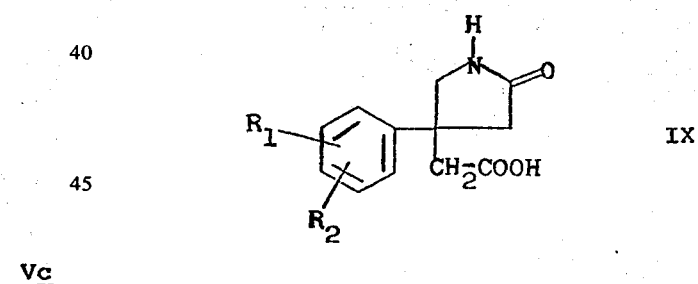

IX wherein $R_1$ and $R_2$ are as defined above, with polyphosphoric acid. Cyclization is optionally effected in an inert organic solvent, e.g. an aromatic hydrocarbon such as benzene, at a temperature between 100 and 180°C.

h'. A compound of formula IX may, for example, be obtained by hydrolysis of a compound of formula X, wherein $R_1$, $R_2$ and $R_4$ are as defined above, may, for example, be obtained by reacting a compound of formula V$a$, as described in process ($c$), with a compound of formula IV$b$.

e'. A compound of formula V$a$ may, for example, be obtained by reducing a compound of formula VII,

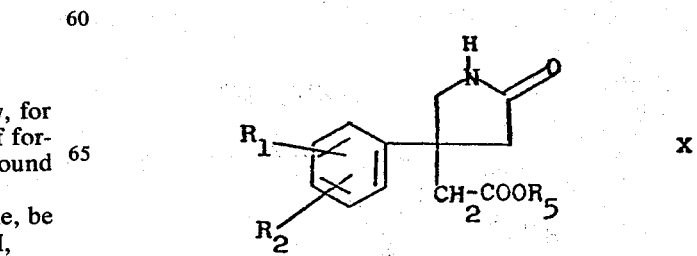

X wherein $R_1$ and $R_2$ are as defined above, and $R_5$ is lower alkyl.

Hydrolysis is preferably effected in an alkaline medium.

i'. A compound of formula X may, for example, be obtained by hydrogenating a compound of formula XI,

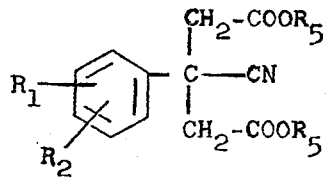

XI wherein $R_1$, $R_2$ and $R_5$ are as defined above, in the presence of a catalyst, with cyclization. Hydrogenation is preferably effected at a temperature between approximately 50° and 100°C, in an autoclave at a hydrogen pressure of approximately 71 to 91 atmospheres, in the presence of an inert organic solvent, e.g. a suitable alcohol, and may have a duration of approximately 10 to 50 hours. An example of a suitable catalyst is Raney nickel.

j'. A compound of formula XI may, for example, be produced by reacting a compound of formula XII,

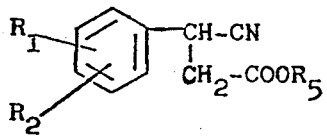

XII wherein $R_1$, $R_2$ and $R_5$ are as defined above, in conventional manner with a bromoacetic acid alkyl ester in the presence of a basic condensation agent.

k'. A compound of formula XII may be obtained by reacting a compound of formula XIII,

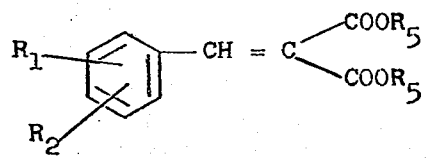

XIII wherein $R_1$, $R_2$ and $R_5$ are as defined above, optionally in the presence of a water-miscible inert organic solvent, e.g. a suitable alcohol of formula XIV, $R_5OH$  XIV wherein $R_5$ is as defined above, with an aqueous alkali metal cyanide solution. The reaction is preferably effected at an elevated temperature, e.g. at a temperature between 40° and 100°C, and may have a duration between 10 and 20 hours.

l'. A compound of formula XIII may, for example, be obtained by reacting a compound of formula XV,

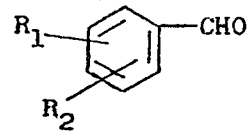

XV wherein $R_1$ and $R_2$ are as defined above, with a malonic acid ester of formula XVI,

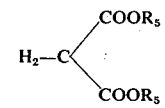

XVI wherein $R_5$ is as defined above, in conventional manner.

Insofar as the production of the starting materials is not particularly described, these are known or may be produced in accordance with known processes, or in a manner analogous to the processes described herein or to known processes.

The compounds of formula I are useful because they possess pharmacological activity in animals. In particular the compounds are useful as analgesics, as indicated by standard tests, for example, in the tail flick test in mice at a dose of approximately 1 to 30 mg/kg animal body weight s.c., and by an inhibition of the phenyl benzoquinone syndrome in mice at a dose of approximately 1.5 to 30 mg/kg animal body weight p.o.

For the abovementioned use, the dosage to be administered will of course vary depending on the compound employed, mode of administration and treatment desired. However, in general, satisfactory results are obtained when administered at a daily dosge of from about 1 to 30 mg/kg animal body weight, orally or parenterally, preferably given in divided doses 2 to 4 times daily or in sustained release form. For the larger mammals the total daily dosage is in the range of from about 50 to 500 mg, and dosage forms suitable for oral administration contain from about 12 to 250 mg of the compound admixed with a solid or liquid pharmaceutical carrier or diluent. p-Fluoro-4-(3-hydroxyspiro[indan-1,3'-pyrrolidin]-1'-yl) butyrophenone has been found to be particularly effective as an analgesic when administered p.o. generally at a dosage of from about 5 to 10 mg/kg animal body weight.

The compounds are furthermore useful as central nervous system depressants, particularly for sedation in the treatment of excitation conditions and sleep disorders, as indicated by standard tests, for example, in the climbing test with mice at a dose of approximately 3 to 30 mg/kg animal body weight, and in the light barrier cage test in mice, to determine the motor activity of the mice, at a dose of approximately 3 to 30 mg/kg animal body weight. The compounds also produce a lowering of rectal temperature in mice at a dose of approximately 30 to 50 mg/kg animal body weight, an effect consistent with compounds having a central nervous system depressant effect.

For the abovementioned further use, the dosage administered will, of course vary depending on the compound employed, mode of administration and treatment desired. However, in general, satisfactory results are obtained when administered at a daily dosage of from about 1 to 50 mg/kg animal body weight, orally or parenterally, preferably given in divided doses 2 to 4 times daily or in sustained release form. For the larger mammals, the total daily dosage is in the range of from about 50 to 500 mg, and dosage forms suitable for oral administration contain 12 to 250 mg of the compound in admixture with a solid or liquid pharmaceutical carrier or diluent. 4-(5-Chloro-3-hydroxyspiro[indan-1,3'-pyrrolidin]-1'-yl)-p-fluorobutyrophenone has been found to be particularly effective in the treatment of excitation conditions and sleep disorders when administered p.o. at a dosage generally of 12.5 mg/kg animal body weight.

The compounds of formula I in free base or pharmaceutically acceptable acid addition salt form may be incorporated in a pharmaceutical composition in association with pharmaceutical carriers or diluents. Suitable forms of composition for oral administration are a tablet and a capsule.

One preferred group of compounds are the compounds of formula I wherein $R_1$ and $R_2$ are hydrogen.

When $R_1$ and $R_2$ are other than hydrogen, then one of the substituents is preferably in the 5 position of the indan nucleus.

$R_3$ in formula I is preferably methylcarboxy or methylcarbamoyloxy.

Free base and pharmaceutically acceptable acid addition salt forms of the compounds of the invention exhibit the same order of activity. Examples of pharmaceutically acceptable acid addition salt forms are the hydrochloride, hydrobromide, sulphate, hydrogen fumarate, malonate and naphthalene-1,5-disulphonate.

The invention is illustrated with reference to the following Examples, wherein all temperatures are indicated in degrees Centigrade. Unless otherwise indicated, the title compounds in the Examples are obtained as a mixture of diastereoisomeric forms.

EXAMPLE 1 p-Fluoro-4-(3-hydroxyspiro[indan-1,3'-pyrrolidin]-1'-yl) butyrophenone

A. 15 g of spiro[indan-1,3'-pyrrolidin]-3-ol are dissolved in 200 cc of dimethyl formamide, and the solution is heated to 100° with 18 g of sodium carbonate and 23 g of 2-(3-chloropropyl)-2-(p-fluorophenyl)-1,3'-dioxolane for 20 hours. Filtration is subsequently effected, the filter residue is washed with 150 cc of chloroform, and the organic phases are concentrated. The 2-[3-(3-hydroxyspiro[indan-1,3'-pyrrolidin]-1'-yl)propyl]-2-(p-fluorophenyl)-1,3-dioxolane obtained as yellow oil is taken up in 300 cc of chloroform without previous purification and is stirred with 250 cc of 2 N hydrochloric acid at room temperature for 1½ hours. The reaction mixture is subsequently rendered alkaline with caustic soda solution, is extracted thrice with 100 cc amounts of chloroform, and the chloroform phase is concentrated. The crude title compound is obtained as brown oil, to which a solution of 8 g of fumaric acid in 150 cc of ethanol is added. After the addition of some ether, the hydrogen fumarate of the title compound is obtained. M.P. 174°–176° (from ethanol/ether).

B. 8.5 g of spiro[indan-1,3'-pyrrolidin]-3-ol, 12.0 g of 4-chloro-p-fluorobutyrophenone and 11.5 g of sodium carbonate are heated at reflux in 100 cc of dimethyl formamide while stirring for 20 hours. After cooling, filtration is effected, the filtrate is evaporated to dryness, taken up in 300 cc of chloroform and extracted thrice with 50 cc amounts of 2 N hydrochloric acid. The acid extract is rendered alkaline with 2 N caustic soda solution while cooling and extraction is effected with chloroform. The crude title compound, obtained as oil after concentrating the chloroform phase by evaporation, is converted into the hydrogen fumarate with fumaric acid. The hydrogen fumarate of the title compound has a M.P. of 174°–176° (from ethanol/ether).

C. 1RS, 3SR-p-Fluoro-4-(3-hydroxyspiro[indan-1,3'-pyrrolidin]-1'-yl) butyrophenone Nuclear magnetic resonance measurements with the use of an europium complex indicate that the hydrogen fumarate of the title compound obtained in accordance with Example 1 (A) or 1 (B), having a M.P. of 174°–176°, is a mixture of diastereoisomers, which contains 30 % of the 1RS,3RS isomer, and 70 % of the 1RS,3SR isomer. 12 g of this mixture are dissolved in ethanol, and a small amount of ether is added. The compound which crystallizes slowly is sterically pure, as indicated by its nuclear magnetic resonance spectrum, and is the hydrogen fumarate of 1RS,3SR-p-fluoro-4-(3-hydroxyspiro[indan-1,3'-pyrrolidin]-1'-yl) butyrophenone, having a M.P. of 183°.

D. 1RS,3RS-p-Fluoro-4-(3-hydroxyspiro[indan-1,3'-pyrrolidin]-1'-yl) butyrophenone The mother liquor obtained in Example 1 (C) is concentrated, 50 cc of chloroform are added to the residue and this is shaken thoroughly with 50 cc of a 2 N caustic soda solution. The crude 1RS,3RS-p-fluoro-4-(3-hydroxyspiro[indan-1,3'-pyrrolidin]-1'-yl) butyrophenone, obtained after concentrating the chloroform phase which has been washed and dried over magnesium sulphate, is purified by chromatography on silica gel, and 20 cc of ethanol saturated with hydrogen chloride gas are added. After the addition of some ether, the hydrochloride of the 1RS,3RS isomer, having a M.P. of 210°–211°, crystallizes.

The starting material may be produced as follows:

a. 200 g of malonic acid diethyl ester, 144 g of benzaldehyde, 14 cc of piperidine and 11.7 g of benzoic acid are heated in 400 cc of benzene for 14 hours at water separating reflux (bath temperature 130°–140°, water separation about 25 cc). After cooling, 200 cc of benzene are added and washing is successively effected twice with 200 cc amounts of water, twice with 200 cc amounts of 1 N hydrochloric acid and 100 cc of a saturated sodium bicarbonate solution, and the benzene is removed by distillation on a rotary evaporator. The resulting benzalmalonic acid diethyl ester is purified by distillation. B.P. 143°–152°/0.2 mm Hg, B.P. 127°–134°/0.1 mm Hg.

b. 120 g of benzalmalonic acid diethyl ester, 33.6 g of potassium cyanide, 1600 cc of ethanol and 160 cc of water are stirred at a bath temperature of 60° for 12 to 14 hours. The reaction mixture is then cooled with ice water, the potassium bicarbonate which crystallizes is filtered off, the filtrate is made neutral with about 15 cc of 1 N hydrochloric acid, air is passed through the solution with a water jet vacuum pump for 1 hour, the solvent is distilled off on a rotary evaporator, 100 cc of water are added to the oily residue, and extraction is effected 6 times with 250 cc amounts of ether. The 3-cyano-3-phenyl-propionic acid ethyl ester, obtained after distilling off the ether, is purified by vacuum distillation. B.P. 125°–130°/0.15 mm Hg.

c. 42 g of sodium amide suspended in 400 cc of absolute ether are added dropwise at room temperature to a solution of 158 g of 3-cyano-3-phenylpropionic acid ethyl ester and 144 g of bromoacetic acid ethyl ester in 1 liter of absolute ether. After adding about half of the suspension, the reaction solution has a light brown colour and starts to boil. After the dropwise addition is complete, the reaction solution is heated at reflux for 2 hours, is cooled, the excess sodium amide is decomposed by the careful dropwise addition of water, the ether solution is washed with 250 cc of 2 N hydrochloric acid and 250 cc of water and is concentrated by evaporation. The resulting 3-cyano-3-phenylglutaric acid diethyl ester is purified by vacuum distillation. B.P. 172°–175°/0.08 mm Hg.

d. 45 g of Raney nickel are added to 254.2 g of 3-cyano-3-phenylglutaric acid diethyl ester in 1.5 liters of absolute methanol, and hydrogenation is effected in a 5 liter autoclave for 30 hours at 80° and a hydrogen pressure of 81 atmospheres. After cooling, the catalyst is filtered off, the filtrate is concentrated on a rotary evaporator, the resulting light yellow oil is taken up in 1.5 liters of chloroform and is successively washed with 25 cc of 2 N hydrochloric acid, 100 cc of saturated sodium bicarbonate solution and 100 cc of water. The 5-oxo-3-phenyl-3-pyrrolidine acetic acid ethyl ester, obtained after concentrating the chloroform phase, crystallizes upon triturating with ether. M.P. 49°–51° (from ethyl acetate/petroleum ether).

e. 195 g of 5-oxo-3-phenyl-3-pyrrolidine acetic acid ethyl ester are dissolved in a mixture of 200 cc of water, 47 g of sodium hydroxide and 750 cc of ethanol while stirring at room temperature. After allowing to stand at room temperature for 1 hour, the sodium salt of 5-oxo-3-phenyl-3-pyrrolidine acetic acid crystallizes. It is dissolved in 600 cc of water and acidified with about 600 cc of 2 N hydrochloric acid while cooling with ice, whereby 5-oxo-3-phenyl-3-pyrrolidine acetic acid separates in crystalline form. M.P. 186°–188° (from ethanol).

f. 200 g of polyphosphoric acid are heated to 160°; 20 g of 5-oxo-3-phenyl-3-pyrrolidine acetic acid are rapidly added while stirring, and the mixture is kept at this temperature for 3,5′minutes. The mixture is then cooled and poured on 800 g of ice, is extracted 10 times with 150 cc amounts of chloroform, and the chloroform phase is concentrated in a vacuum. The resulting spiro[indan-1,3′-pyrrolidin]-3,5′-dione which becomes crystalline upon triturating and seeding, is recrystallized from 70 to 80 cc of ethanol. M.P. 152°–153°.

g. 17.1 g of lithium aluminium hydride in 300 cc of absolute tetrahydrofuran and 600 cc of absolute benzene are placed in a Soxhlet apparatus. 30 g of the spiro[indan-1,3′-pyrrolidin]-3,5′-dione to be reduced are placed in the Soxhlet apparatus in a Soxhlet capsule. Boiling at reflux is then effected for 20 hours, whereby the entire product is dissolved. The reaction mixture is subsequently cooled and carefully decomposed with 25 cc of water in 25 cc of tetrahydrofuran, the precipitate is filtered off and the filtrate concentrated. Spiro[indan-1,3′-pyrrolidin]-3-ol is obtained as light yellow oil and is converted into its hydrogen fumarate by reacting with a solution of 17 g of fumaric acid in 400 cc of ethanol. M.P. 155°–158° (from ethanol/ether).

EXAMPLE 2 p-Fluoro-4-(3-hydroxy-6-methoxyspiro[indan-1,3′-pyrrolidin]-1′-yl) butyrophenone A. 15 g of 6-methoxyspiro[indan-1,3′-pyrrolidin]-3-ol (mixture of diastereoisomers) and 15 g of 4-chloro-p-fluorobutyrophenone are heated to the boil in 300 cc of absolute toluene. 22 g of sodium carbonate are added in small portions within 30 minutes, and a further 10 g of sodium carbonate are added after 20 hours, and the mixture is boiled at reflux for a total of 30 hours. After cooling filtration is effected, the filter residue is boiled with chloroform, and the combined organic phases are concentrated by evaporation. The resulting crude, light brown, oily title compound is converted into the hydrogen fumarate with fumaric acid. The hydrogen fumarate of the title compound (mixture of diastereoisomers 35:65) has a M.P. of 163°–165° (from ethanol/ether).

B. 15 g of 6-methoxyspiro[indan-1,3′-pyrrolidin]-3-ol and 22 g of 2-(3-chloropropyl)-2-(p-fluorophenyl)-1,3′-dioxolane are reacted in accordance with the process described in Example 1(A). The hydrogen fumarate of the title compound has a M.P. of 163°–165° (from ethanol/ether).

The starting material may be produced as follows:

a. m-Methoxybenzalmalonic acid diethyl ester, produced in a manner analogous to that described in Example 1(a). B.P. 140°–150°/0.05 mm Hg, M.P. 45°.

b. 3-Cyano-3-(m-methoxyphenyl)propionic acid ethyl ester, produced in a manner analogous to that described in Example 1(b). B.P. 140°–150°/0.3 mm Hg.

c. 3-Cyano-3-(m-methoxyphenyl)glutaric acid diethyl ester, produced in a manner analogous to that described in Example 1(c). B.P. 163°–168°/0.2 mm Hg.

d. 3-(m-Methoxyphenyl)-5-oxo-3-pyrrolidine acetic acid ethyl ester, produced in a manner analogous to that described in Example 1(d). The crude compound obtained as viscous oil is used for the next reaction without purification.

e. 3-(m-Methoxyphenyl)-5-oxo-3-pyrrolidine acetic acid, produced in a manner analogous to that described in Example 1(e). The alkaline reaction solution is shaken thoroughly once with 100 cc of methylene chloride in order to remove the byproducts of hydrogenation. Extraction is then effected once with 750 cc of 2N hydrochloric acid and 5 times with 150 cc amounts of methylene chloride, the methylene chloride phases are concentrated and the resulting compound is recrystallized from ethanol. M.P. 144°–146°.

f. 3-(m-Methoxyphenyl)-5-oxo-3-pyrrolidine acetic acid is reacted in a manner analogous to that described in Example 1(f). The resulting yellow, oily crude product is a mixture of isomers of 6-methoxyspiro[indan-1,3′-pyrrolidin]-3,5′-dione and 4-methoxyspiro[indan-1,3′-pyrrolidin]-3,5′-dione. Upon adding about 20 cc of ethanol, 6-methoxyspiro[indan-1,3′-pyrrolidin]-3,5′-dione crystallizes in the form of white crystals. M.P. 225°.

g. 6-Methoxyspiro[indan-1,3′-pyrrolidin]-3-ol, produced in a manner analogous to that described in Example 1(g), from 6-methoxyspiro[indan-1,3′-pyr-

EXAMPLE 3

4-(6-Chloro-3-hydroxyspiro[indan-1,3'-pyrrolidin]-1'-yl)-p-fluorobutyrophenone

6-Chlorospiro[indan-1,3'-pyrrolidin]-3-ol (mixture of diastereoisomers) is reacted in a manner analogous to that described in Example 1(A) or Example 2(A). The crude, light brown oily title compound is purified by chromatography on silica gel and is subsequently converted into the hydogen fumarate. The hydrogen fumarate of the title compound (mixture of diastereoisomers) has a M.P. of 165°–167° (from methanol/ether).

The starting material may be obtained as follows:

a. m-Chlorobenzalmalonic acid diethyl ester, produced in a manner analogous to that described in Example 1(a). B.P. 138°–139°/0.3 mm Hg.

b. 3-(m-Chlorophenyl)-3-cyanopropionic acid ethyl ester, produced in a manner analogous to that described in Example 1(b). B.P. 158°–162°/0.5 mm Hg.

c. 3-(m-Chlorophenyl)-3-cyanoglutaric acid diethyl ester, produced in a manner analogous to that described in Example 1(c). B.P. 166°–171°/0.4 mm Hg.

d. 3-(m-Chlorophenyl)-5-oxo-3-pyrrolidine acetic acid ethyl ester, produced in a manner analogous to that described in Example 1(d). The crude product is used for the next reaction without purification.

e. 3-(m-Chlorophenyl)-5-oxo-3-pyrrolidine acetic acid, produced in a manner analogous to that described in Example 2(e). M.P. 178°–181°.

f. 3-(m-Chlorophenyl)-5-oxo-3-pyrrolidine acetic acid is reacted in a manner analogous to that described in Example 1(f). Reaction time 15 minutes. The reaction mixture is extracted with methylene chloride. The crystalline product obtained after concentrating the methylene chloride phase by evaporation, is a mixture of isomers of 6-chlorospiro[indan-1,3'-pyrrolidin]-3,5'-dione and 4-chlorospiro[indan-1,3'-pyrrolidin]-3,5'-dione. The two isomers are separated by fractional crystallization from methylene chloride/ethanol. 6-Chlorospiro[indan-1,3'-pyrrolidin]-3,5'-dione has a M.P. of 210°–220°. 4-Chlorospiro[indan-1,3'-pyrrolidin]-3,5'-dione has a M.P. of 176°–179°.

g. 25 g of 6-chlorospiro[indan-1,3'-pyrrolidin]-3,5'-dione are dissolved in 100 cc of dimethyl formamide and 250 cc of methanol, and a suspension of 2 g of sodium borohydride in 50 cc of water and 5 drops of caustic soda solution are added dropwise at room temperature. The temperature is kept at 25° by cooling. The solution is stirred for an hour at aluminum temperature, is then poured on water and extracted several times with chloroform. The mixture of the diastereoisomeric forms of 6-chloro-3-hydroxy[indan-1,3'-pyrrolidin]carefully 5'-one, obtained after concentrating the chloroform phase by evaporation, is used as such for the next reaction. diastereoisomeric h. A solution of 25 g of 6-chloro-3-hydroxyspiro[indan-1,3'-pyrrolidin]-5'-one in 100 cc of ether and 100 cc of tetrahydrofuran is added dropwise to a suspension of 8.5 g of lithium aluminium hydride in 200 cc of tetrahydrofuran and 200 cc of ether. The mixture is boiled at reflux for 20 hours, is then carefully decomposed with 75 cc of water, filtration is effected, and the organic phases are concentrated. The resulting yellow oil is a mixture of the diastereoisomeric forms of 6-chlorospiro[indan-1,3'-pyrrolidin]-3-ol and is used for the next reaction without further purification.

EXAMPLE 4

4-(4-Chloro-3-hydroxyspiro[indan-1,3'-pyrrolidin]-1'-yl)-p-fluorobutyrophenone

4-Chlorospiro[indan-1,3'-pyrrolidin]-3-ol (mixture of diastereoisomers) is reacted in a manner analogous to that described in Example 1(A) or Example 2(A). After purifying the crude product by chromatography on silica gel, the diastereoisomeric forms of the title compound are obtained as oils. After recrystallization from methanol/ether, the hydrogen fumarates of the diastereoisomers of the title compound have a M.P. of 161°–163° or 190°–192°.

The starting material is obtained from 4-chlorospiro[indan-1,3'-pyrrolidin]-3,5'-dione [production see Example 3(f)] in a manner analogous to that described in Example 3(g) to 3(h).

EXAMPLE 5

4-(5-Chloro-3-hydroxyspiro[indan-1,3'-pyrrolidin]-1'-yl)-p-fluorobutyrophenone

5-Chlorospiro[indan-1,3'-pyrrolidin]-3-ol is reacted in a manner analogous to that described in Example 1(A) or Example 2(A). The hydrogen fumarate of the title compound has a M.P. of 148°–149°.

The starting material may be obtained as follows:

a. p-Chlorobenzalmalonic acid diethyl ester, produced in a manner analogous to that described in Example 4(a). B.P. 135°–142°/0.2 mm Hg.

b. 3-(p-Chlorophenyl)-3-cyanopropionic acid ethyl ester, produced in a manner analogous to that described in Example 1(b). B.P. 141°–145°/0.3 mm Hg.

c. 3-(p-Chlorophenyl)-3-cyanoglutaric acid diethyl ester, produced in a manner analogous to that described in Example 1(c). B.P. 166°–169°/0.3 mm Hg.

d. 3-(p-Chlorophenyl)-5-oxo-3-pyrrolidine acetic acid ethyl ester, produced in a manner analogous to that described in Example 1(d). The crude product is used as such for the next reaction.

e. 3-(p-Chlorophenyl)-5-oxo-3-pyrrolidine acetic acid, produced in a manner analogous to that described in Example 2(e). M.P. 190°–191°.

f. 5-Chlorospiro[indan-1,3'-pyrrolidin]-3,5'-dione, produced in a manner analogous to that described in Example 1(f). M.P. 220°–222°.

g. 5-Chloro-3-hydroxyspiro[indan-1,3'-pyrrolidin]-5'-one, produced in a manner analogous to that described in Example 3(g). M.P. 172°–174°.

h. 5-Chlorospiro[indan-1,3'-pyrrolidin]-3-ol, produced in a manner analogous to that described in Example 3(h). The crude product is used as such for the next reaction.

EXAMPLE 6 p-Fluoro-4-(3-hydroxy-4-methoxyspiro[indan-1,3'-pyrrolidin]-1'-yl)-butyrophenone 4-Methoxyspiro[indan-1,3'-pyrrolidin]-3-ol is reacted in a manner analogous to that described in Example 1(A) or Example 2(A). The hydrogen fumarate of the title compound has a M.P. of 152°–154° (from ethanol/ether).

The 4-methoxyspiro[indan-1,3'-pyrrolidin]-3-ol, M.P. 184°–186°, required as starting material, is obtained in a manner analogous to that described in Example 2(g), from 4-methoxyspiro[indan-1,3'-pyrrolidin]-3,5'-dione, M.P. 184°–186°, which is obtained from the mother liquor resulting after crystallizing the 6-methoxyspiro[indan-1,3'-pyrrolidin]-3,5'-dione in Example 2(f).

EXAMLE 7 p-Fluoro-4-(3-hydroxy-6-methylspiro[indan-1,3'-pyrrolidin]-1'-yl) butyrophenone

6-Methylspiro[indan-1,3'-pyrrolidin]-3-ol is reacted in a manner analogous to that described in Example 1(A) or Example 12(A). The hydrogen fumarate of the title compound has a M.P. of 172°–174° (from ethanol/ether).

The starting material may be obtained as follows:

a. m-Methylbenzalmalonic acid diethyl ester, produced in a manner analogous to that described in Example 1(a). B.P. 135°–140°/0.4 mm Hg.

b. 3-Cyano-3-(m-tolyl)propionic acid ethyl ester, produced in a manner analogous to that described in Example 1(b). B.P. 143°–148°/0.1 mm Hg.

c. 3-Cyano-3-(m-tolyl)glutaric acid diethyl ester, produced in a manner analogous to that described in Example 1(c). B.P. 160°–167°/0.08 mm Hg.

d. 5-Oxo-3-(m-tolyl)-3-pyrrolidine acetic acid ethyl ester, produced in a manner analogous to that described in Example 1(d). The crude product is used as such for the next reaction.

e. 5-Oxo-3-(m-tolyl)-3-pyrrolidine acetic acid, produced in a manner analogous to that described in Example 2(e). M.P. 152°–154°.

f. 6-Methylspiro[indan-1,3'-pyrrolidin]-3,5'-dione, produced in a manner analogous to that described in Example 1(f). M.P. 188°–192°.

g. 3-Hydroxy-6-methylspiro[indan-1,3'-pyrrolidin]-5'-one, produced in a manner analogous to that described in Example 3(g), used for the next reaction as crude product.

h. 6-Methylspiro[indan-1,3'-pyrrolidin]-3-ol, produced in a manner analogous to that described in Example 3(h), used for the next reaction as crude product.

EXAMPLE 8 p-Fluoro-4-(5-fluoro-3-hydroxyspiro[indan-1,3'-pyrrolidin]-1'-yl) butyrophenone

5-Fluorospiro[indan-1,3'-pyrrolidin]-3-ol is reacted in a manner analogous to that described in Example 1(A) or Example 2(A). The hydrogen fumarate of the title compound has a M.P. of 143°–145° (from ethanol/ether).

The starting material may be obtained as follows:

a. p-Fluorobenzalmalonic acid diethyl ester, produced in a manner analogous to that described in Example 1(a). B.P. 149°–153°/0.9 mm Hg.

b. 3-Cyano-3-(p-fluorophenyl)propionic acid ethyl ester, produced in a manner analogous to tht described in Example 1(b). B.P. 146°–160°/0.5 mm Hg.

c. 3-Cyano-3-(p-fluorophenyl)glutaric acid diethyl ester, produced in a manner analogous to that described in Example 1(c). M.P. 68°–70° (from ether/petroleum ether).

d. 3-(p-Fluorophenyl)-5-oxo-3-pyrrolidine acetic acid ethyl ester, produced in a manner analogous to that described in Example 1(d). The crude compound obtained as a viscous oil is used as such for the next reaction.

e. 3-(p-Fluorophenyl)-5-oxo-3-pyrrolidine acetic acid, produced in a manner analogous to that described in Example 2(e). M.P. 174°–176°.

f. 5-Fluorospiro[indan-1,3'-pyrrolidin]-3,5'-dione, produced in a manner analogous to that described in Example 1(f). M.P. 198°–202°.

g. 5-Fluorospiro[indan-1,3'-pyrrolidin]-3-ol, produced in a manner analogous to that described in Example 1(g). The crude compound is converted into the hydrogen fumarate. M.P. 162°–164° (from ethanol/ether).

EXAMPLE 9 p-Fluoro-4-(3-hydroxy-5-methoxyspiro[indan-1,3'-pyrrolidin]-1'-yl) butyrophenone 5-Methoxyspiro[indan-1,3'-pyrrolidin]-3-ol (mixture of diastereoisomers) is reacted in a manner analogous to that described in Example 1(A) or Example 2(A). The hydrogen fumarate of the title compound (mixture of diastereoisomers 70:30) has a M.P. of 113°–115° (from ethanol/ether).

The starting material may be obtained as follows:

a. p-Methoxybenzalmalonic acid diethyl ester, produced in a manner analogous to that described in Example 1(a). B.P. 145°–160°/0.5 mm Hg.

b. 3-Cyano-3-(p-methoxyphenyl)propionic acid ethyl ester, produced in a manner analogous to that described in Example 1(b). B.P. 190°–200°/0.3 mm Hg.

c. 3-Cyano-3-(p-methoxyphenyl)glutaric acid diethyl ester, produced in a manner analogous to that described in Example 1(c). M.P. 65°–75° (from ether/petroleum ether).

d. 3-(p-Methoxyphenyl)-5-oxo-3-pyrrolidine acetic acid ethyl ester, produced in a manner analogous to that described in Example 1(d). The compound is used in crude state for the next reaction.

e. 3-(p-Methoxyphenyl)-5-oxo-3-pyrrolidine acetic acid, produced in a manner analogous to that described in Example 2(e). M.P. 172°–175°.

f. 5-Methoxyspiro[indan-1,3'-pyrrolidin]-3,5'-dione, produced in a manner analogous to that described in Example 1(f). M.P. 179°–180°.

g. 5-Methoxyspiro[indan-1,3'-pyrrolidin]-3-ol, produced in a manner analogous to that described in Example 1(g). The crude compound (mixture of diastereo-isomers) is used for the next reaction without purification.

EXAMPLE 10 p-Fluoro-4-(3-hydroxy-5-methylspiro[indan-1,3'-pyrrolidin]-1'-yl) butyrophenone

5-Methylspiro[indan-1,3'-pyrrolidin]-3-ol (mixture of diastereoisomers) is reacted in a manner analogous to that described in Example 1(A) or Example 2(A). The hydrogen fumarate of the title compound (mixture of diastereoisomers 25:75) has a M.P. of 163°–164° (from ethanol/ether).

The starting material may be obtained as follows:

a. p-Methylbenzalmalonic acid ethyl ester, produced in a manner analogous to that described in Example 1(a). B.P. 160°–167°/0.4 mm Hg.

b. 3-Cyano-3-(p-tolyl)propionic acid ethyl ester, produced in a manner analogous to that described in Example 1(b). B.P. 145°–155°/0.3 mm Hg.

c. 3-Cyano-3-(p-tolyl)glutaric acid diethyl ester, produced in a manner analogous to that described in Example 1(c). B.P. 185°–190°/0.5 mm Hg.

d. 5-Oxo-3-(p-tolyl)-3-pyrrolidine acetic acid ethyl ester, produced in a manner analogous to that described in Example 1(d). The compound is used in crude state for the next reaction.

e. 5-Oxo-3-(p-tolyl)-3-pyrrolidine acetic acid, produced in a manner analogous to that described in Example 2(e). M.P. 184°–186°.

f. 5-Methylspiro[indan-1,3'-pyrrolidin]-3,5'-dione, produced in a manner analogous to that described in Example 1(f). M.P. 162°–164°.

g. 5-Methylspiro[indan-1,3'-pyrrolidin]-3-ol, produced in a manner analogous to that described in Example 1(g). The compound (mixture of diastereoisomers) is used in crude state for the next reaction.

EXAMPLE 11

4-(5,7-dichloro-3-hydroxyspiro[indan-1,3'-pyrrolidin]-1'-yl)-p-fluorobutyrophenone 5,7-Dichlorospiro[indan-1,3'-pyrrolidin]-3-ol is reacted in a manner analogous to that described in Example 1(A) or Example 2(A). The hydrogen fumarate of the title compound has a M.P. of 149°–152° (from ethanol/ether).

The starting material may be obtained as follows:

a. 2,4-Dichlorobenzalmalonic acid diethyl ester, produced in a manner analogous to that described in Example 1(a). B.P. 172°–178°/0.4 mm Hg.

b. 3-(2,4-Dichlorophenyl)-3-cyanopropionic acid ethyl ester, produced in a manner analogous to that described in Example 1(b). B.P. 180°–185°/0.5 mm Hg.

c. 3-(2,4-Dichlorophenyl)-3-cyanoglutaric acid diethyl ester, produced in a manner analogous to that described in Example 1(c). The compound is used in crude state for the next reaction.

d. 3-(2,4-Dichlorophenyl)-5-oxo-3-pyrrolidine acetic acid ethyl ester, produced in a manner analogous to that described in Example 1(d). The compound is used in crude state for the next reaction.

e. 3-(2,4-Dichlorophenyl)-5-oxo-3-pyrrolidine acetic acid, produced in a manner analogous to that described in Example 2(e). M.P. 188°–192° (from ethanol/ether).

f. 5,7-Dichlorospiro[indan-1,3'-pyrrolidin]-3,5'-dione, produced in a manner analogous to that described in Example 1(f). M.P. 226°–228°.

g. 5,7-Dichlorospiro[indan-1,3'pyrrolidin]-3-ol, produced in a manner analogous to that described in Example 1(g). Light yellow oil, which is used for the next reaction without purification.

EXAMPLE 12

4-(4,5-Dichloro-3-hydroxyspiro[indan-1,3'-pyrrolidin]-1'-yl)-p-fluorobutyrophenone 4,5-Dichlorospiro[indan-1,3'-pyrrolidin]-3-ol (mixture of diastereoisomers) is reacted in a manner analogous to that described in Example 1(A) or Example 2(A). The hydrogen furmarate of the title compound has a M.P. of 190°–193°.

The starting material may be obtained as follows:

a. 3,4-Dichlorobenzalmalonic acid diethyl ester, produced in a manner analogous to that described in Example 1(a). B.P. 169°–173°/0.5 mm Hg.

b. 3-(3,4-Dichlorophenyl)-3-cyanopropionic acid ethyl ester, produced in a manner analogous to that described in Example 1(b). B.P. 185°–195°/0.5 mm Hg.

c. 3-(3,4-Dichlorophenyl)-3-cyanoglutaric acid diethyl ester, produced in a manner analogous to that described in Example 1(c). White crystals having a M.P. of 65°–67°.

d. 3-(3,4-Dichlorophenyl-5-oxo-3-pyrrolidine acetic acid ethyl ester, produced in a manner analogous to that described in Example 1(d). The crude compound is used for the next reaction without purification.

e. 3-(3,4-Dichlorophenyl)-5-oxo-3-pyrrolidine acetic acid, produced in a manner analogous to that described in Example 2(e). M.P. 191-195°.

f. 4,5-Dichlorospiro[indan-1,3'-pyrrolidin]-3,5'-dione, produced in a manner analogous to that described in Example 1 (f). The crystalline product obtained after recrystallization from ethanol contains a small amount of impurities of 5,6-dichlorospiro-[indan1,3'-pyrrolidin]-3,5'-dione, and has a M.P. of 202°–205°. It is used as such for the next reaction.

g. 4,5-Dichlorospiro[indan-1,3'-pyrrolidin]-3-ol, produced in a manner analogous to that described in Example 1(g). The crude compound is converted into its hydrogen fumarate with a solution of fumaric acid in ethanol. M.P. 167°–170°.

EXAMPLE 13

4-(3-Hydroxy-5,6-dimethoxyspiro[indan-1,3'-pyrrolidin]-1'-yl)-p-fluorobutyrophenone 5,6-Dimethoxyspiro[indan-1,3'-pyrrolidin]-3-ol is reacted in a manner analogous to that described in Example 1(A) or Example 2(A).

A solution of naphthalene-1,5-disulphonic acid in ethanol is added to the crude oily title compound, whereby the naphthalene-1,5-disulphonate of the title compound crystallizes and has a M.P. of 146°–148° after recrystallization from ethanol.

The starting material may be obtained as follows:

a. 3,4-Dimethoxybenzalmalonic acid ethyl ester, produced in a manner analogous to that described in Example 1(a). B.P. 190°–210°/0.1 mm Hg.

b. 3-Cyano-3-(3,4-dimethoxyphenyl)propionic acid ethyl ester, produced in a manner analogous to that described in Example 1(b). B.P. 205°–212°/0.3 mm Hg.

c. 3-Cyano-3-(3,4-dimethoxyphenyl)glutaric acid diethyl ester, produced in a manner analogous to that described in Example 1(c). B.P. 215°–225°/0.1 mm Hg.

d. 3-(3,4-Dimethoxyphenyl)-5-oxo-3-pyrrolidine acetic acid ethyl ester, produced in a manner analogous to that described in Example 1(d). The compound is used for the next reaction in crude state.

e. 3-(3,4-Dimethoxyphenyl)-5-oxo-3-pyrrolidine acetic acid, produced in a manner analogous to that described in Example 2(e). M.P. 162°–165°.

f. 5,6-Dimethoxyspiro[indan-1,3'-pyrrolidin]-3,5'-dione, produced in a manner analogous to that described in Example 1 (f). M.P. 193°–195°.

g. 5,6-Dimethoxyspiro[indan-1,3'-pyrrolidin]-3-ol, produced in a manner analogous to that described in Example 1(g). Yellow oil, which is used as such for the next reaction.

In analogous manner to that described in the preceding example, the compound 4-(3-hydroxy-5,6-methylenedioxyspiro[indan-1,3'-pyrrolidin]-1'-yl)-p-fluoro-butyrophenone may be produced.

EXAMPLE 14

4-(3-Hydroxy-5-isopropylspiro[indan-1,3'-pyrrolidin]-1'-yl)-p-fluorobutyrophenone 5-Isopropylspiro[indan-1,3'-pyrrolidin]-3-ol (mixture of diastereoisomers) is reacted in a manner analogous to that described in Example 12 or Example 2 (A), and the title compound is converted into its hydrogen fumarate having a M.P. of 167°–174°.

The starting material may be obtained as follows:

a. 4-Isopropylbenzalmalonic acid ethyl ester, produced in a manner analogous to that described in Example 1(a). B.P. 152°–154°/0.4 mm Hg.

b. 3-Cyano-3-(4-isopropylphenyl)propionic acid ethyl ester, produced in a manner analogous to that described in Example 1(b). B.P. 146°–149°/0.1 mm Hg.

c. 3-Cyano-3-(4-isopropylphenyl)glutaric acid diethyl ester, produced in a manner analogous to that described in Example 1(c). B.P. 166°–190°/0.2-0.4 mm Hg.

d. 3-(4-Isopropylphenyl)-5-oxo-3-pyrrolidine acetic acid ethyl ester, produced in a manner analogous to that described in Example 1(d). The compound is used for the next reaction in crude state.

e. 3-(4-Isopropylphenyl)-5-oxo-3-pyrrolidine acetic acid, produced in a manner analogous to that described in Example 2(e). M.P. 175°–178°.

f. 5-Isopropylspiro[indan-1,3'-pyrrolidin]-3,5'-dione, produced in a manner analogous to that described in Example 1(f). M.P. 165°–167°.

g. 5-Isopropylspiro[indan-1,3'-pyrrolidin]-3-ol, produced in a manner analogous to that described in Example 1(g). Yellow oil, which is used as such for the next reaction.

EXAMPLE 15

4-(3-Hydroxy-5,7-dimethylspiro[indan-1,3'-pyrrolidin]-1'-yl)-p-fluorobutyrophenone 5,7-Dimethylspiro[indan-1,3'-pyrrolidin]-3-ol is reacted in a manner analogous to that described in Example 1(A) or Example 2(A), and the title compound is converted into its hydrogen fumarate having a M.P. of 164°–167°.

The starting material may be obtained as follows:

a. 2,4-Dimethylbenzalmalonic acid ethyl ester, produced in a manner analogous to that described in Example 1(a). B.P. 138°–141°/0.15 mm Hg.

b. 3-Cyano-3-(2,4-dimethylphenyl)propionic acid ethyl ester, produced in a manner analogous to that described in Example 1(b). B.P. 140°–150°/0.25–0.35 mm Hg.

c. 3-Cyano-3-(2,4-dimethylphenyl)glutaric acid diethyl ester, produced in a manner analogous to that described in Example 1(c). B.P. 180°–190°/0.15 mm Hg.

d. 3-(2,4-Dimethylphenyl)-5-oxo-3-pyrrolidine acetic acid ethyl ester, produced in a manner analogous to that described in Example 1(d). Is used for the next reaction in crude state.

e. 3-(2,4-Dimethylphenyl)-5-oxo-3-pyrrolidine acetic acid, produced in a manner analogous to that described in Example 2 (e). M.P. 225°–230°.

f. 5,7-Dimethylspiro[indan-1,3'-pyrrolidin]-3,5'-dione, produced in a manner analogous to that described in Example 1(f). M.P. 208°–210°.

g. 5,7-Dimethylspiro[indan-1,3'-pyrrolidin]-3-ol, produced in a manner analogous to that described in Example 1(g). Yellow oil, which is used as such for the next reaction.

EXAMPLE 16

1RS,3RS-p-Fluoro-4-(3-hydroxyspiro[indan-1,3'-pyrrolidin]-1'-yl) butyrophenone

1RS,3RS-Spiro[indan-1,3'-pyrrolidin]-3-ol is reacted in accordance with the process described in Example 1(A) or 1(B). A solution of hydrochloric acid in ethanol is added to the crude title compound, and the hydrochloride of the title compound is crystallized by the addition of some ether. M.P. 210°–211°.

The starting material may be obtained as follows:

a. Spiro[indan-1,3'-pyrrolidin]-3,5'-dione is reduced in a manner analogous to that described in Example 3(g) with sodium borohydride. The resulting 3hydroxyspiro[indan-1,3'-pyrrolidin]-5'-one is a mixture of diastereoisomers having a M.P. of 120°–130°, which contains about 50 % of the 1RS,3RS isomer and about 50 % of the 1RS,3SR isomer. 30 g of the crude mixture are extracted thrice with 100 cc amounts of chloroform at the boil. 1RS,3RS-3-hydroxyspiro[indan-1,3'-pyrrolidin]-5'-one, having a M.P. of 150°–152°, is obtained as extraction residue and is further reduced with lithium aluminium hydride in a manner analogous to that described in Example 3(h).

1RS,3SR-3-Hydroxyspiro[indan-1,3'-pyrrolidin]-5'-one, having a M.P. of 120-123°, crystallizes from the chloroform solution after the addition of ether.

EXAMPLE 17

1RS,3SR-p-Fluoro-4-(3-hydroxyspiro[indan-1,3'-pyrrolidin]-1'-yl) butyrophenone

1RS,3SR-Spiro[indan-1,3'-pyrrolidin]-3-ol is reacted in a manner analogous to that described in Example 1(A) or 1(B). The hydrogen fumarate of the title compound has a M.P. of 183° (from ethanol/ether).

The starting material may be obtained by reducing the 1RS,3SR-3-hydroxyspiro[indan-1,3'-pyrrolidin]-5'-one, obtained in Example 16(a), in a manner analogous to that described in Example 3(h).

EXAMPLE 18

4-(3-Acetoxyspiro[indan-1,3'-pyrrolidin]-1'-yl)-p-fluorobutyrophenone 7.5 g of p-fluoro-4-(3-hydroxyspiro[indan-1,3'-pyrrolidin]-1'-yl)butyrophenone are stirred at room temperature with 15 cc of pyridine and 15 cc of acetic anhydride for 18 hours. The mixture is then poured on ice, is rendered alkaline with 2 N caustic soda solution and is extracted thrice with 50 cc of ether. The ether phase is washed with water, dried over sodium sulphate and concentrated by evaporation. The oily residue is converted into the hydrogen fumarate, which is recrystallized from ethanol/ether. The hydrogen fumarate of the title compound has a M.P. of 154°–156°.

EXAMPLE 19 p-Fluoro-4-(3-methylcarbamoyloxyspiro[indan-1,3'-pyrrolidin]-1'-yl) butyrophenone 9.0 g of p-fluoro-4-(3-hydroxyspiro[indan-1,3'-pyrrolidin]-1'-yl) butyrophenone and 2.0 g of methyl isocyanate are dissolved in 50 cc of methylene chloride. After allowing the reaction solution to stand at room temperature for 20 hours, it is concentrated by evaporation, and the resulting oil is converted into the hydrogen fumarate. After recrystallization from ethanol/ether, the hydrogen fumarate of the title compound has a M.P. of 167°–169°.

EXAMPLE 20 p-Fluoro-4-(5-methyl-3-propionyloxyspiro[indan-1,3'-pyrrolidin]-1'-yl) butyrophenone p-Fluoro-4-(3-hydroxy-5-methylspiro[indan-1,3'-pyrrolidin]-1'-yl) butyrophenone is reacted with propionic acid anhydride in a manner analogous to that described in Example 18. The hydrogen fumarate of the title compound has a M.P. of 153°–155° (from ethanol/ether).

EXAMPLE 21

4-(5-Chloro-3-methylcarbamoylspiro[indan-1,3'-pyrrolidin]-1'-yl)-p-fluorobutyrophenone 4-(5-Chloro-3-hydroxyspiro[indan-1,3'-pyrrolidin]-1'-yl)-p-fluorobutyrophenone is reacted with methyl isocyanate in chloroform in a manner analogous to that described in Example 19. Reaction time 24 hours at the boil. The hydrogen fumarate of the title compound has a M.P. of 151°–153° (from ethanol/ether).

EXAMPLE 22

2-[3-(3-Hydroxyspiro[indan-1,3'-pyrrolidin]-1'-yl)propyl]-2-(p-fluorophenyl)-1,3-dioxolane 15 g of spiro[indan-1,3'-pyrrolidin]-3-ol are dissolved in 200 cc of dimethyl formamide and heated to 100° for 20 hours with 18 g of sodium carbonate and 23 g of 2-(3-chloropropyl)-2-(p-fluorophenyl)-1,3'-dioxolane. Filtration is subsequently effected, the filter residue is washed with 150 cc of chloroform and the organic phases are concentrated. The title compound obtained as yellow oil is purified by chromatography. Thin layer chromatogram: Rf value 0.600 (adsorbent: silica gel, eluant: benzene/ethanol/ammonia 15:4:0:2).

The hydrogen fumarate of p-fluoro-4-(3-hydroxyspiro[indan-1,3'-pyrrolidin]-1'-ol) butyrophenone, obtained by hydrolysis of the ketal group of the title compound, has a M.P. of 174°–176° (from ethanol/ether).

Hydrolysis is effected by dissolving the title compound in 300 cc of chloroform and stirring at room temperature for 1½ hours with 250 cc of 2 N hydrochloric acid. The solution is then made alkaline with caustic soda solution, the chloroform phase is separated, and the crude p-fluoro-4-(3-hydroxyspiro[indan-1,3'-pyrrolidin]-1'-yl) butyrophenone, obtained after concentrating the chloroform phase, is converted into the hydrogen fumarate with fumaric acid.

In analogous manner to that described in the preceding Example, 2-[3-(3-hydroxyspiro[indan-1,3'-pyrrolidin]-1'-yl)propyl]-2-(p-fluorophenyl)-1,3-dioxane may be produced.

The following compounds of formula Ig may be produced in a manner analogous to that described in Example 22 and may be characterized by the melting point of the hydrogen fumarate of the butyrophenone derivative obtained by hydrolysis of the compound:

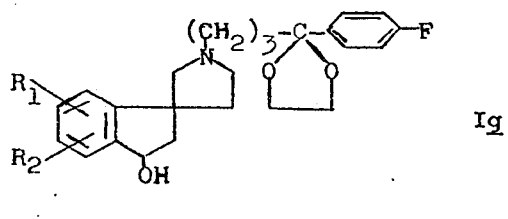

| Example No. | R₁ | R₂ | Rf value (thin layer chromatogram on silica gel, eluant: benzene/ethanol/ammonia 15 : 4 : 0.2) | M.P. of the hydrogen fumarate of the butyrophenone derivative |
|---|---|---|---|---|
| 23 | 5-Cl | H | 0.700 | 148–149° (ethanol/ether) |
| 24 | 4-CH₃O | H | 0.610 | 152–154° (ethanol/ether) |
| 25 | 6-CH₃O | H | 0.645 | 163–165° (ethanol/ether) |
| 26 | 4-Cl | H | 0.570 | 178–180° (ethanol/ether) |
| 27 | 6-Cl | H | 0.630 | 165–167° (ethanol/ether) |
| 28 | 6-CH₃ | H | 0.590 | 181–183° (ethanol/ether) |
| 29 | 5-CH₃O | H | 0.680 | 113–115° (ethanol/ether) |
| 30 | 5-F | H | 0.610 | 143–145° (ethanol/ether) |
| 31 | 5-CH₃ | H | 0.530 | 163–164° (ethanol/ether) |
| 32 | 4-Cl | 5-Cl | 0.790 | 190–193° (ethanol/ether) |
| 33 | 5-Cl | 7-Cl | 0.675 | 149–152° (ethanol/ether) |

EXAMPLE 34

4-(3-Acetoxyspiro[indan-1,3'-pyrrolidin]-1'-yl)-p-fluorobutyrophenone

3-Acetoxyspiro[indan- 1,3'-pyrrolidine] is reacted in a manner analogous to that described in Example 1 (B). The crude title compound obtained as an oil is converted into its hydrogen fumarate with fumaric acid and is recrystallized from ethanol/ether. M.P. 154°–156°.

The starting material may be obtained as follows:

a. 56.0 g of 1'-benzyl-3-hydroxyspiro[indan-1,3'-pyrrolidine] are stirred at room temperature with 120 cc of pyridine and 120 cc of acetic anhydride for 20 hours. The mixture is then poured on ice, is made alkaline with 2 N caustic soda solution and is extracted thrice with 250 cc amounts of ether. The ether phase is washed with water, dried over sodium sulphate and concentrated by evaporation. 1'-Benzyl-3-acetoxyspiro[indan-1,3'-pyrrolidine] is obtained as light yellow oil, which is used for the next reaction without purification.

b. 30.0 g of the product obtained above are dissolved in 300 cc of ethanol, 3.0 g of palladium charcoal are added, and hydrogenation is effected at 50° and a hydrogen pressure of 76 atmospheres for 12 hours. Filtration is effected, the ethanol is distilled off, and 3- acetoxyspiro[indan-1,3'-pyrrolidine] is obtained as residue in the form of an almost colourless oil, which is used as such for the next reaction.

EXAMPLE 35 p-Fluoro-4-(3-methylcarbamoyloxyspiro[indan-1,3'-pyrrolidin]-1'-yl) butyrophenone 3-Methylcarbamoyloxyspiro[indan-1,3'-pyrrolidine] is reacted in a manner analogous to that described in Example 1 (B), and the title compound is converted into its hydrogen fumarate. M.P. 167°–169° (from ethanol/ether).

The starting material may be obtained as follows:

A. 56.0 g of 1'-benzyl-3-hydroxyspiro[indan-1,3'-pyrrolidine] and 10.0 g of methyl isocyanate are dissolved in 500 cc of methylene chloride. After allowing the reaction solution to stand at room temperature for 20 hours, the solvent is distilled off. The resulting oily 1'-benzyl-3-methylcarbamoyl-oxyspiro[indan-1,3'-pyrrolidine] is used for the next reaction without purification.

B. 250 g of the product obtained above are dissolved in 300 cc of ethanol, and hydrogenation is effected in the presence of 3.0 g of palladium charcoal at 50° and a hydrogen pressure of 51 atmospheres for 15 hours. The catalyst is then filtered off, the ethanol is removed by distillaton, and 3-methylcarbamoyloxyspiro[indan-1,3'-pyrrolidine] is obtained as residue. The oily product is used for the next reaction without further purification.

EXAMPLE 36

(1RS,3RS)-4-(5-chloro-3-hydroxyspiro-[indane-1,3'-pyrrolidin]-1'yl)-p-fluorobutyrophenone 15 g of 5-chlorospiro[indane-1,3'-pyrrolidin]-3-ol (mixture of diastereoismers of 50 % of the 1RS,3SR and 50 % of the 1RS,3RS isomer) are dissolved in 200 cc of dimethyl formamide and heated to 100° for 6 hours together with 18 g of sodium carbonate and 23 g of 2-(3-chloropropyl)-2-(p-fluorophenyl)-1,3-dioxolane. Filtration is subsequently effected, the filter residue is washed with chloroform and the organic phase is concentrated. The resulting yellow oil is taken up in 300 cc of chloroform and stirred at room temperature for 1 hour with 250 cc of 2 N hydrochloric acid. The reaction mixture is subsequently made alkaline with caustic soda solution while cooling, is extracted with chloroform and the chloroform phase is concentrated. The crude title compound is obtained together with the 1RS,3SR isomer as brown oil. After adding a solution of hydrogen chloride in ethanol, the 1RS,3RS form crystallizes alone. The hydrochloride form of the pure title compound has a M.P. of 203°–206° after recrystallization from ethanol/ether.

In analogous manner Example 36 is repeated using 2-(3-chloropropyl)-2-(p-fluorophenyl)-1,3-dioxane whereupon the intermediate compound obtained is the title compound in 1,3-dioxane form instead of in 1,3-dioxolane form. The intermediate may be purified if desired in conventional manner.

EXAMPLE 37

(1RS,3SR)-4-(5-chloro-3-hydroxyspiro-[indane-1,3'-pyrrolidin]-1'-yl)-p-fluorobutyrophenone 15 g of (1RS,3SR)-5-chlorospiro[indane-1,3'-pyrrolidin]-3-ol in 200 cc of dimethyl formamide are heated to 100° for 6 hours together with 18 g of sodium carbonate and 23 g of 2-(3-chloropropyl)-2-(p-fluorophenyl)-1,3-dioxolane. Filtration is subsequently effected, the filter residue is washed with chloroform and the organic phase is concentrated. The resulting yellow oil is taken up in 300 cc of chloroform and stirred at room temperature for 1 hour with 250 cc of 2 N hydrochloric acid. The reaction mixture is subsequently made alkaline with caustic soda solution while cooling, the chloroform phase is separated and concentrated. After the addition of a solution of fumaric acid in alcohol, the hydrogen fumarate form of the title compound crystallizes. M.P. 154°–156° from ethanol/ether.

The starting material may be obtained as follows:

a. 210 g of 5-chlorospiro[indane-1,3'-pyrrolidine]-3,5'-dione are dissolved in 2,5 liters of methanol, and a solution of 20 g of sodium borohydride in 250 cc of water and 5 cc of caustic soda solution is added at room temperature at such a rate that the temperature in the reaction vessel does not exceed 25°. The solution is stirred at room temperature for 2 hours, is then poured on ice and extracted several times with chloroform. The 5-chloro-3-hydroxyspiro[indane-1,3'-pyrrolidin]-5'-one, obtained after concentrating the chloroform solution by evaporation, is a mixture of diastereoisomers, having a M.P. of 155°–180°, and containing approximately equal parts of the 1RS,3SR and the 1RS,3RS isomer. Pure (1RS,3SR)-5-chloro-3-hydroxyspiro[indane-1,3'-pyrrolidin]-5'-one, having a M.P. of 213°–216°, may be obtained by extracting repeatedly with chloroform and subsequently recrytallizing twice from methanol.

b. A solution of 25 g of (1RS,3SR)-5-chloro-3-hydroxyspiro[indane-1,3'-pyrrolidin]-5'-one in 100 cc of tetrahydrofuran is added dropwise to a suspension of 8 g of lithium aluminum hydride in 200 cc of tetrahydrofuran and 200 cc of ether. The mixture is boiled at reflux for 20 hours, is then carefully decomposed with 75 cc of water, filtration is effected and the organic phase is concentrated. The (1RS,3SR)-5-chlorospiro-[indane-1,3'-pyrrolidin]-3-ol, obtained as yellow oil, is used for the next reaction without further purification.

EXAMPLE 38

(1RS,3SR)-p-fluoro-4-(3-hydroxy-5-methylspiro[indane-1,3'-pyrrolidin]-1'-yl)butyrophenone (1RS,3SR)-5-methylspiro[indane-1,3'-pyrrolidin]-3-ol is reacted in a manner analogous to that described in Example 37 M.P. of the hydrogen fumarate form of the title compound: 173°–175°.

The starting material is obtained in a manner analogous to that described in Example 37(a) and 37(b), by reduction of 5-methylspiro[indane-1,3'-pyrrolidine]-3,5'-dione with sodium borohydride, removal of the 1RS,3RS isomer from the reaction product and subsequent reduction with lithium aluminum hydride.

EXAMPLE 39

(1RS,3RS)-p-fluoro-4-(3-hydroxy-5-methylspiro[indane-1,3'-pyrrolidin]-1'-yl)butyrophenone Crude (1RS,3RS)-5-methylspiro[indane-1,3'-pyrrolidin]-3-ol (containing approximately 20 % of the 1RS,3SR isomer) is reacted in a manner analogous to that described in Example 36. Hydrochloric acid in ethanol is added to the crude title compound, containing impurities of the 1RS,3SR isomer, whereby the hydrochloride form of the sterically uniform title compound crystallizes after the addition of some ether. M.P. 137°–139°.

EXAMPLE 40

(1RS,3RS)-4-(3-acetoxyspiro[indane-1,3′-pyrrolidin]-1′-yl)-p-fluorobutyrophenone 7.5 g of (1RS,3RS)-p-fluoro-4-(3-hydroxy-spiro[indane-1,3′-pyrrolidin]-1′-yl)butyrophenone are stirred at room temperature for 20 hours together with 15 cc of pyridine and 15 cc of acetic anhydride. The reaction mixture is then poured on ice, is made alkaline with 2 N caustic soda solution and is extracted thrice with 100 cc amounts of ether. The crude title compound obtained as oily residue after concentrating the ether phase by evaporation, is converted into the hydrogen fumarate form, which is recrystallized from ethanol/ether. M.P. of the hydrogen fumarate form of the title compound: 168°–170°.

The following esters are produced in a manner analogous to that described in Example 40, by reaction of the corresponding p-fluoro-4-(3-hydroxy-spiro[indane-1,3′-pyrrolidin]-1′-yl)butyrophenone with a corresponding acid anhydride.

EXAMPLE 41

(1RS,3RS)-p-fluoro-4-(3-propionyloxyspiro-[indane-1,3′-pyrrolidin]-1′-yl)butyrophenone M.P. of the hydrogen fumarate form: 151°–152°.

EXAMPLE 42

(1RS,3RS)-4-[3-(2,2-dimethylpropionyloxy-spiro[indane-1,3′-pyrrolidin]-1′-yl)]-p-fluorobutyrophenone M.P. of the hydrogen fumarate form: 147°–148°.

EXAMPLE 43

(1RS,3RS)-p-fluoro-(5-methyl-3-propionyloxyspiro[indane-1,3′-pyrrolidin]-1′-yl)butyrophenone M.P. of the hydrogen fumarate form: 180°–181°.

EXAMPLE 44

(1RS,3SR)-p-fluoro-(5-methyl-3-propionyloxyspiro[indane-1,3′-pyrrolidin]-1′-yl)butyrophenone M.P. of the hydrogen fumarate form: 168°–169°.

EXAMPLE 45

The diastereoisomeric mixture of Example 15 is chromatographed on silica gel using benzene/ethanol as diluent to separate the two isomers:

(1RS, 3RS) 4-(3-hydroxy-5,7-dimethylspiro[indan-1,3′-pyrrolidin]-1′-yl)-p-fluorobutyrophenone, m.pt. 128°–130° (hydrogen fumarate) (1RS, 3SR) 4-(3-hydroxy-5,7-dimethylspiro[indan-1,3′-pyrrolidin]-1′yl)-p-fluorobutyrophenone, m.pt. 166°–167° (hydrogen fumarate).

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

We claim:

1. A method of treating pain in animals which comprises administering to an animal in need of such treatment an analgesic effective amount of a compound of the formula

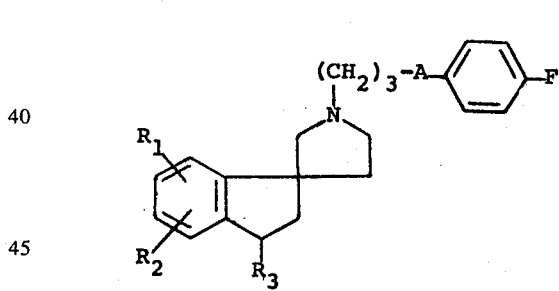

wherein
$R_1$ is hydrogen, alkyl of 1 to 3 carbon atoms, fluorine, chlorine, bromine or methoxy,
$R_2$ is hydrogen, alkyl of 1 to 3 carbon atoms, chlorine or methoxy, or
$R_1$ and $R_2$ are ortho one to another and together form a methylene dioxy group,
$R_3$ is hydroxy, alkylcarboxy of 2 to 5 carbon atoms or monoalkylcarbamoyloxy of 2 to 5 carbon atoms, and
A is carbonyl, 1,3-dioxolan-2-ylidene or 1,3-dioxan-2-ylidene,
in free base or pharmaceutically acceptable acid addition salt form thereof.

2. A method of claim 1 wherein $R_1$ and $R_2$ of formula I are each hydrogen.

3. A method of claim 1 wherein one of $R_1$ and $R_2$ of formula I is other than hydrogen and is in the 5-position of the indan nucleus.

4. A method of claim 1 wherein $R_3$ of formula I is methylcarboxy or methylcarbamoyloxy.

5. A method of claim 1 using the compound in 1RS, 3RS racemic form.

6. A method of claim 1 using the compound in 1RS, 3SR racemic form.

7. A method of claim 1 using the compound which is p-fluoro-4-(3-hydroxyspiro [indan-1,3-pyrrolidin]-1'-yl) butyrophenone.

8. A method of claim 1 using the compound which is p-fluoro-4-(5-methyl-3-propionyloxyspiro-[indan-1,3'-pyrrolidin]-1'-yl) butyrophenone.

9. A method of claim 1 using the compound which is (1RS,3RS)-p-fluoro-4-(3-hydroxyspiro[indan-1,3'-pyrrolidin]-1'-yl)-butyrophenone.

10. A method of claim 1 using the compound which is (1RS,3SR)-p-fluoro-4-(3-hydroxyspiro[indan-1,3'-pyrrolidin]-1'-butyrophenone.

11. A method of claim 1 using the compound which is (1RS,3RS)-p-fluoro-(5-methyl-3-propionyloxy-spiro[indane-1,3'-pyrrolidin]-1'-yl)butyrophenone.

12. A method of claim 1 using the compound which is (1RS,3SR)-p-fluoro-(5-methyl-3-propionyloxy-spiro[indan-1,3'-pyrrolidin]-1'-butyrophenone.

13. A method of claim 1 wherein a compound is used which is an individual (1RS,3RS) or (1RS,3SR) compound of formula

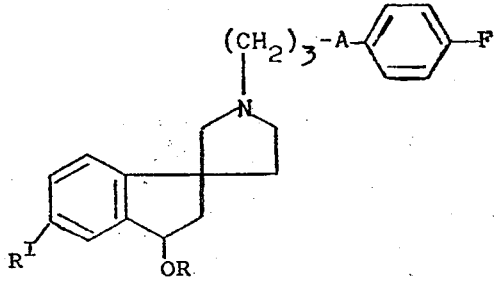

wherein

R is hydrogen, or $R_3{}^I$—CO—, wherein $R_3{}^I$ is lower alkyl,
i. when R is hydrogen, $R^I$ is chlorine or methyl, or,
ii. when R is $R_3{}^I$—CO—, $R^I$ is hydrogen or methyl, and A is carbonyl, 1,3-dioxolan-2-ylidene or 1,3-dioxan-2-ylidene 14. A method of claim 1 wherein A is carbonyl.

15. A method of claim 1 wherein A is 1,3-dioxolan-2-ylidene, or 1,3-dioxan-2-ylidene.

16. A method of claim 14 wherein $R_2$ is hydrogen.

17. A method of claim 16 wherein $R_1$ is hydrogen, alkyl, chlorine or methoxy.

18. A method of claim 17 wherein $R_3$ is hydroxy, alkylcarboxy or monoalkylcarbamoyloxy.

19. A method of claim 14 wherein $R_3$ is hydroxy.

20. A method of claim 14, wherein $R_3$ is alkylcarboxy.

21. A method of claim 14, wherein $R_1$ and $R_2$ are independently hydrogen, chlorine, alkyl or methoxy.

22. A method of claim 1, wherein $R_1$ and $R_2$ are independently hydrogen, alkyl, chlorine, fluorine, or methoxy and A is carbonyl or 1,3-dioxolan-2-ylidene.

23. A method according to claim 1, wherein from about 1 to about 30 mg/kg animal body weight is administered daily.

24. A method according to claim 23, wherein from about 50 to about 500 mg animal body weight is administered daily.

25. A method according to claim 1, wherein p-fluoro-4-(3-hydroxyspiro[indan-1,3'-pyrrolidin]-1'-yl)butyrophenone is administered at a daily dosage of from 5 to 10 mg/kg animal body weight.

26. A method of simultaneously sedating and treating conditions of pain in animals which comprises administering to an animal in need of such treatment a therapeutically effective amount of a compound of the formula

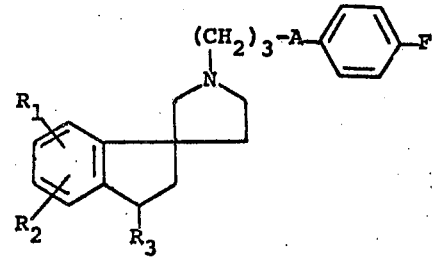

wherein
$R_1$ is hydrogen, alkyl of 1 to 3 carbon atoms, fluorine, chlorine, bromine or methoxy,
$R_2$ is hydrogen, alkyl of 1 to 3 carbon atoms, chlorine or methoxy, or
$R_1$ and $R_2$ are ortho one to another and together form a methylene dioxy group,
$R_3$ is hydroxy, alkylcarboxy of 2 to 5 carbon atoms or monoalkylcarbamoyloxy of 2 to 5 carbon atoms, and
A is carbonyl, 1,3-dioxolan-2-ylidene or 1,3-dioxan-2-ylidene,
in free base or pharmaceutically acceptable acid addition salt form thereof.

27. A method of treating excitation conditions in animals which comprises administering to an animal in need of such treatment a therapeutically effective amount of a compound of the formula

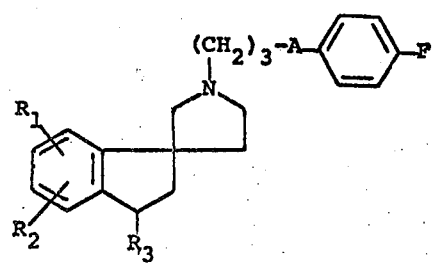

where
$R_1$ is hydrogen, alkyl of 1 to 3 carbon atoms, fluorine, chlorine, bromine or methoxy,
$R_2$ is hydrogen, alkyl of 1 to 3 carbon atoms, chlorine or methoxy, or
$R_1$ and $R_2$ are ortho one to another and together form a methylene dioxy group,
$R_3$ is hydroxy, alkylcarboxy of 2 to 5 carbon atoms or monoalkylcarbamoyloxy of 2 to 5 carbon atoms, and
A is carbonyl, 1,3-dioxolan-2-ylidene or 1,3-dioxan-2-ylidene, in free base or pharmaceutically acceptable acid addition salt form thereof.

28. A method of treating sleep disorders in animals which comprises administering to an animal in need of such treatment a therapeutically effective amount of a compound of the formula

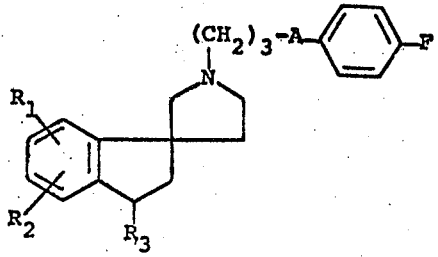

where
R₁ is hydrogen, alkyl of 1 to 3 carbon atoms, fluorine, chlorine, bromine or methoxy,
R₂ is hydrogen, alkyl of 1 to 3 carbon atoms, chlorine or methoxy, or
R₁ and R₂ are ortho one to another and together form a methylene dioxy group,
R₃ is hydroxy, alkylcarboxy of 2 to 5 carbon atoms or monoalkylcarbamoyloxy of 2 to 5 carbon atoms, and
A is carbonyl, 1,3-dioxolan-2-ylidene or 1,3-dioxan-2-ylidene,
in free base or pharmaceutically acceptable acid addition salt form thereof.

29. A pharmaceutical composition having sedating and analgesic activity comprising an effective amount of a compound of the formula

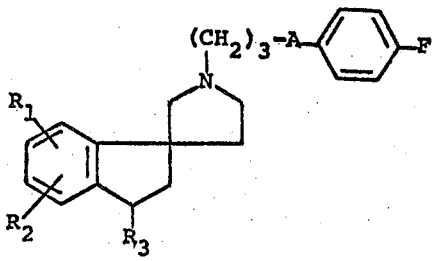

where
R₁ is hydrogen, alkyl of 1 to 3 carbon atoms, fluorine, chlorine, bromine or methoxy,
R₂ is hydrogen, alkyl of 1 to 3 carbon atoms, chlorine or methoxy, or
R₁ and R₂ are ortho one to another and together form a methylene dioxy group,
R₃ is hydroxy, alkylcarboxy of 2 to 5 carbon atoms, and
A is carbonyl, 1,3dioxolan-2-ylidene or 1,3-dioxan-2-ylidene,
in free base or pharmaceutically acceptable acid addition salt form thereof, in association with a pharmaceutical diluent or carrier.

* * * * *